US00PP36488P2

(12) United States Plant Patent
Ranney et al.

(10) Patent No.: US PP36,488 P2
(45) Date of Patent: Feb. 25, 2025

(54) ***VIBURNUM* PLANT NAMED 'NCVX5'**

(50) Latin Name: ***Viburnum awabuki* x *(awabuki* x *sieboldii)***
Varietal Denomination: NCVX5

(71) Applicant: North Carolina State University, Raleigh, NC (US)

(72) Inventors: Thomas Green Ranney, Arden, NC (US); Irene Palmer, Arden, NC (US); Nathan Lynch, Arden, NC (US); Andra Windorf Nus, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/745,850

(22) Filed: Jun. 17, 2024

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

(56) References Cited

PUBLICATIONS

Berger, Garden Design Online, Feb. 12, 2024, 7 pages (Year: 2024).*

* cited by examiner

*Primary Examiner* — Keith O. Robinson
(74) *Attorney, Agent, or Firm* — Cassandra Bright

(57) ABSTRACT

A new and distinct cultivar of *Viburnum* plant named 'NCVX5' is described, characterized by abundant white spring flowers with lustrous, evergreen foliage. Plants have upright habits and dense branching. The new cultivar is a *Viburnum*, typically for ornamental garden use.

3 Drawing Sheets

Latin name of the genus and species: *Viburnum awabuki* x (*awabuki* x *sieboldii*).
Variety denomination: 'NCVX5'.

BACKGROUND OF THE INVENTION

The present invention comprises a new and distinct *Viburnum* hereinafter referred to by the cultivar name 'NCVX5'. This new *Viburnum* was developed in 2012 through a breeding program at a research nursery in Mills River, North Carolina. 'NCVX5' was selected in 2013 from a population of seedlings of the seed parent, unpatented *Viburnum awabuki* '2004-032' crossed with the pollen parent, unpatented *Viburnum* 'H2009-134' (*V. awabuki* 'Chindo' x *V. sieboldii* 'Ironclad').

The first asexual propagation of 'NCVX5' was carried out in July 2015 by rooting stem cuttings at the same research nursery in Mills River, North Carolina, and has been asexually reproduced repeatedly by vegetative cuttings over an 8-year period. 'NCVX5' roots readily from softwood cuttings treated with a basal dip of 3,000-4,000 ppm indole butyric acid (potassium salt) in water. 'NCVX5' has been found to retain its distinctive characteristics through successive asexual propagations.

Date of the first public exposure was on Jun. 27, 2023, in the United States. This was made directly by the inventor or one who obtained the claimed invention directly or indirectly from the inventor. This sale and all public disclosures made between Jun. 27, 2023, and the filing of this application fall within the exception allowed under 102(b)(1).

SUMMARY OF THE INVENTION

The cultivar 'NCVX5' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCVX5'. These characteristics in combination distinguish 'NCVX5' as a new and distinct *Viburnum* cultivar:

1. An upright habit with dense branching.
2. Abundant white flowers in spring.
3. Lustrous evergreen foliage.
4. Cold hardy to USDA zone 6b.

PARENT COMPARISONS

Plants of the new cultivar 'NCVX5' are similar to plants of the seed parent in most horticultural characteristics. However, plants of the new cultivar 'NCVX5' differ in the following:

1. Plants of the new variety are more compact and narrow than plants of the seed parent.
2. Plants of the new variety are more cold-hardy than plants of the seed parent.

Plants of the new cultivar 'NCVX5' could not be compared to plants of the pollen parent as there is no record of its traits.

COMMERCIAL COMPARISON

'NCVX5' can be compared to the commercial variety *Viburnum sieboldii* 'Seneca', unpatented. Plants of the new variety are similar to 'Seneca' in most horticultural characteristics, however, 'NCVX5' differs in the following:

1. Plants of the new variety are more compact and narrow than plants of this comparator.
2. Plants of the new variety are evergreen, while plants of this comparator are deciduous.

BRIEF DESCRIPTION OF THE PHOTOGRAPHS

The accompanying photographs were taken using conventional techniques and although colors may appear different from actual colors due to light reflectance it is as accurate as possible by conventional photographic techniques.

DETAILED BOTANICAL DESCRIPTION

Figure 1:
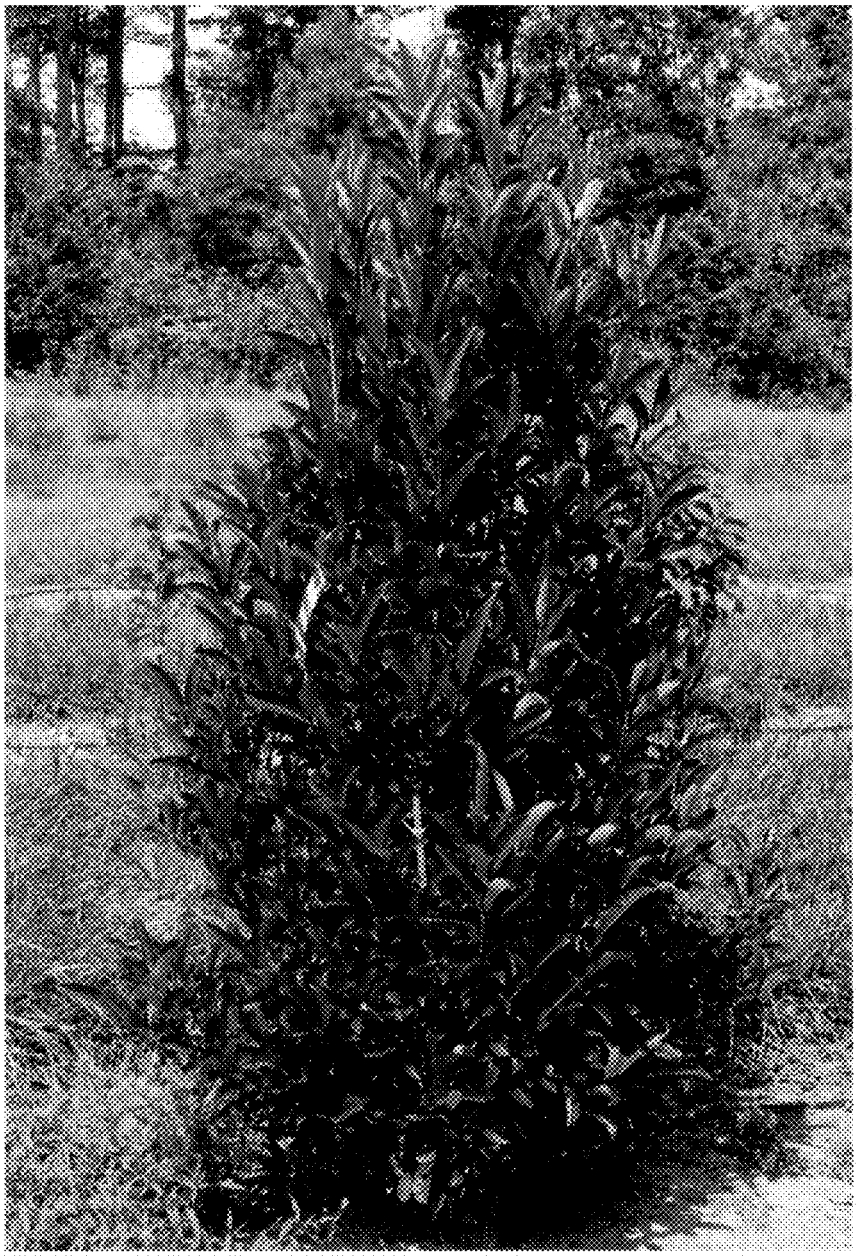
FIG. 1 is a color photograph showing the dense upright habit of a seven-year-old field-grown plant in the summer of 2020, in Mills River, NC.
Figure 2:
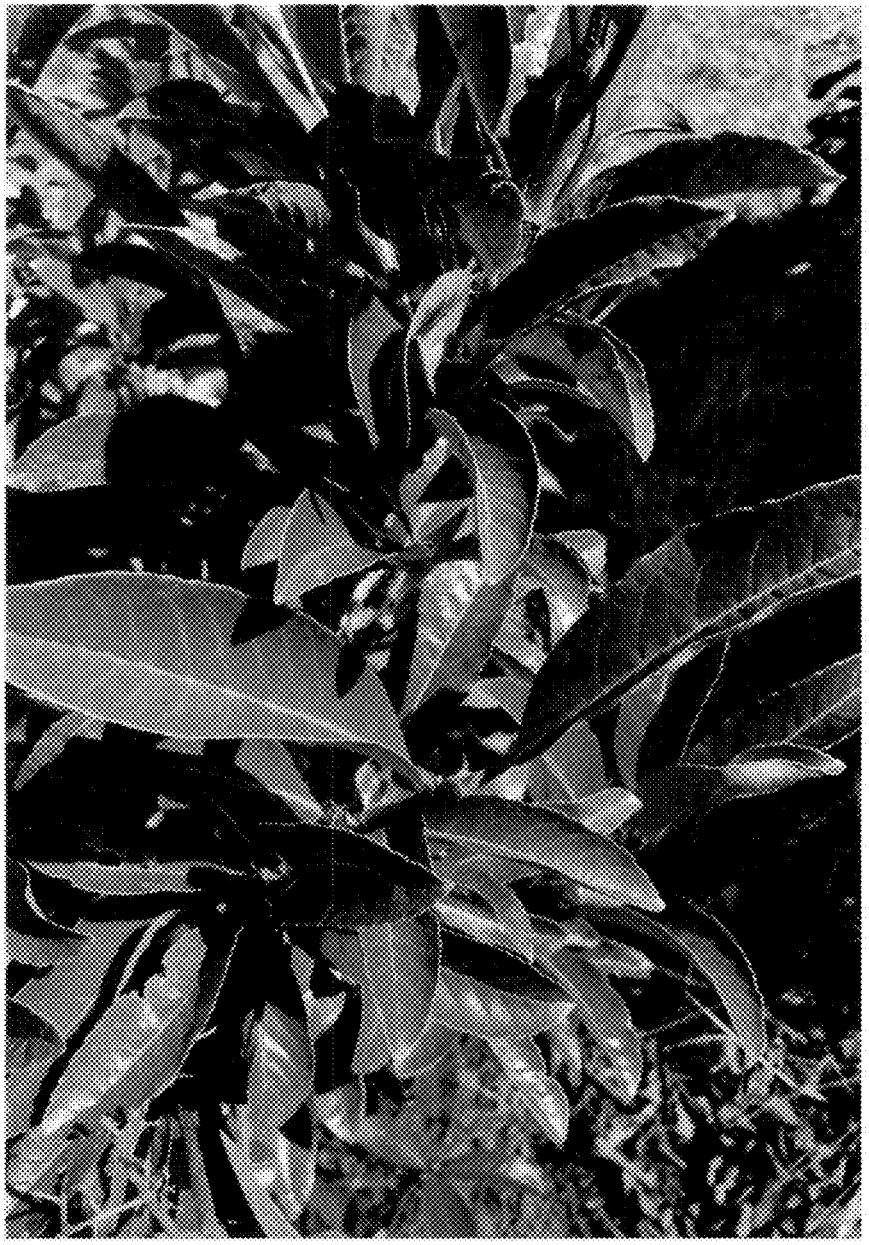
FIG. 2 is a color photograph showing the glossy, dark green foliage of a seven-year-old field-grown plant in summer of 2020, in Mills River, NC.
Figure 3:
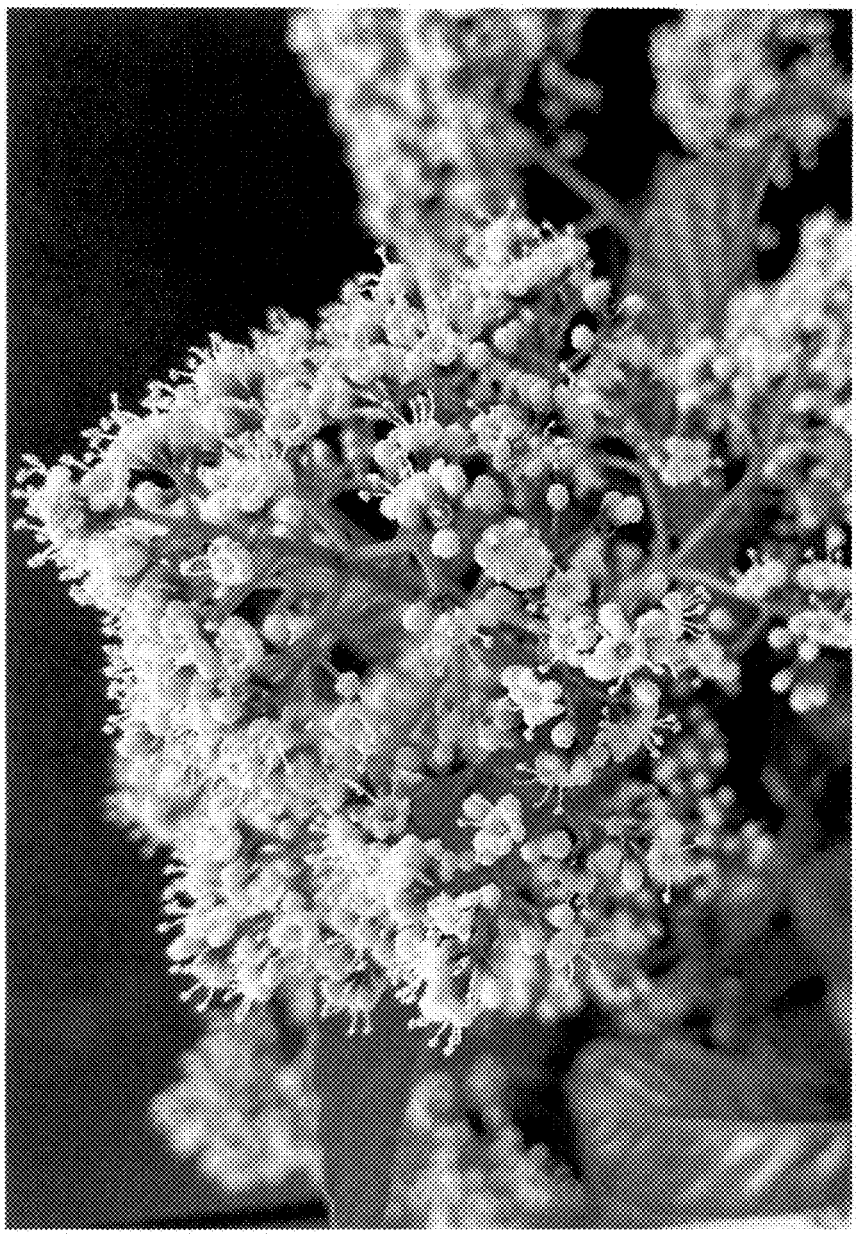
FIG. 3 is a color photograph showing inflorescences of a two-year-old container-grown plant in spring of 2023, in Mills River, NC.

The following is a detailed description of the botanical characteristics of the new and distinct *Viburnum* 'NCVX5'. The detailed description was taken from a seven-year-old field-grown plant in Mills River, NC in 2020, and supplemented with data taken from a two-year-old container-grown plant in Mills River, NC in 2023. All colors cited herein refer to The Royal Horticultural Society Colour Chart (R.H.S.), London, Sixth Edition. Where specific dimensions, sizes, colors, and other characteristics are given, it is to be understood that such characteristics are approximations or averages set forth as accurately as practicable.

Botanical classification: *Viburnum awabuki* x (*awabuki* x *sieboldii*) 'NCVX5'.

PROPAGATION

Method: Softwood cuttings.
Time to initiate roots: 30 days at 18° to 27° C. in summer.
Time to produce rooted young plant: 60 days in summer.
Root description: Dense, freely branched, thin to thick, and fibrous. White in color, not accurately measured using R.H.S. chart.

PLANT

Age of plant described: 2 to 7 years old.
Plant type: Fully evergreen shrub.
Plant shape: Columnar.
Plant vigor: High.
Growth habit: Densely branched and upright.
Growth rate: Moderate to rapid.
Height: 3 to 4 m.
Plant spread: 1 to 1.5 m.
Branching habit: Basal.
Branches (woody branches 2 years and older):
- *Length*.—About 70 cm.
- *Diameter*.—About 1.3 cm.
- *Color*.—RHS Grey-Brown 199B.
- *Texture*.—Glabrous with lenticels of RHS Brown N200A.

Shoots (current year's growth):
- *Length*.—30 to 45 cm.
- *Diameter*.—About 0.5 cm.
- *Color*.—RHS Yellow-Green 144C.
- *Texture*.—Sparsely pubescent.
- *Strength*.—Moderate to Strong.

Internode length: Average 5.6 cm.

FOLIAGE

Leaf:
- *Arrangement*.—Opposite, simple.
- *Persistence*.—Evergreen.
- *Length*.—Average 13 cm.
- *Width*.—Average 5 cm.
- *Shape*.—Ovate-lanceolate.
- *Apex*.—Acute.
- *Base*.—Cuneate.
- *Margin*.—Serrate.
- *Texture*.—Top surface: Glabrous, lustrous, leathery. Bottom surface: Pubescent.
- *Color*.—Upper side: RHS Green NN137B. Under side: RHS Yellow-Green N148A.
- *Venation*.—Type: Pinnate. Color: Upper side: RHS Yellow-Green RHS 144C. Under side: RHS Yellow-Green RHS 144C.
- *Petiole*.—Length: About 1.5 cm. Diameter: About 0.3 cm. Texture: Both sides pubescent. Color: RHS Grey-Brown N199C.

FLOWER

Natural flowering season: Late April to May in Mills River, NC.
Inflorescence type: Single salverform flowers arranged on terminal cymes.
Inflorescence height: About 12 cm.
Inflorescence diameter: About 15 cm.
Quantity of flowers: More than 100 per inflorescence.
Fragrance: Mild, citrusy fragrance.
Longevity on the plant: 1-2 weeks.
Persistence: Self-cleaning.
Bud:
- *Length*.—About 0.8 cm.
- *Diameter*.—About 0.3 cm.
- *Color*.—RHS Yellow-Green 146C.
- *Shape*.—Oblong.
- *Texture*.—Glabrous.

Flower:
- *Length*.—Average 1.4 cm.
- *Width*.—Average 0.6 cm.
- *Shape*.—Single whorl stellate.
- *Aspect*.—Upright and outwardly facing.

Petals:
- *Number*.—5 fused petals.
- *Arrangement*.—Whorled.
- *Length*.—Average 0.2 cm.
- *Width*.—Average 0.1 cm.
- *Shape*.—Ovate.
- *Apex*.—Obtuse.
- *Base*.—Fused.
- *Margin*.—Entire.
- *Texture*.—Glabrous, upper and lower surfaces.
- *Color*.—RHS White NN155B.

Sepals:
- *Number*.—5 fused sepals.
- *Arrangement*.—Whorled.
- *Length*.—About 0.4 cm.

*Width*.—About 0.3 cm.
*Shape*.—Ovate.
*Apex*.—Acute.
*Base*.—Fused.
*Margin*.—Entire.
*Texture*.—Slightly pubescent, upper and lower surfaces.
*Color*.—RHS Yellow-Green 146B.

Peduncles:
*Length*.—Average 6.4 cm.
*Diameter*.—About 0.1 cm.
*Color*.—RHS Yellow-Green 146C.
*Texture*.—Pubescent.
*Strength*.—Moderate.

Pedicels:
*Length*.—Average 0.5 cm.
*Diameter*.—About 0.1 cm.
*Color*.—RHS Yellow-Green 146C.
*Texture*.—Pubescent.
*Strength*.—Moderate.

REPRODUCTIVE ORGANS

Gynoecium:
*Pistil number*.—1.
*Pistil length*.—About 0.2 cm.
*Style length*.—About 0.1 cm.
*Style color*.—RHS Yellow-Green 146D.
*Stigma shape*.—Irregular.
*Stigma color*.—RHS Yellow-Green 146D.

Androecium:
*Stamen number*.—5.
*Anther shape*.—Oblong.
*Anther size*.—About 0.1 cm.
*Anther color*.—RHS White NN155B.
*Amount of pollen*.—Average.
*Pollen color*.—RHS White 155A.

FRUIT AND SEED

Fruit:
*Type*.—Drupe.
*Shape*.—Ovate.
*Length*.—About 1.0 cm.
*Width*.—About 0.5 cm.
*Color*.—RHS Red 42A, maturing to Black 203A.
*Texture*.—Glabrous.

Seed:
*Number per fruit*.—1.
*Shape*.—Ovate.
*Length*.—About 1.0 cm.
*Width*.—About 0.5 cm.
*Color*.—RHS Yellow 18D.
*Texture*.—Glabrous.

OTHER CHARACTERISTICS

Disease/pest resistance: Neither resistance nor susceptibility to the normal pests and diseases of *Viburnum* has been observed.

Cold hardiness: At least USDA zone 6b; testing has not been completed in colder zones.

What is claimed is:

1. A new and distinct cultivar of *Viburnum* plant named 'NCVX5', substantially as illustrated and described herein.

* * * * *